United States Patent [19]

Barry et al.

[11] Patent Number: 5,571,453
[45] Date of Patent: Nov. 5, 1996

[54] STABILIZED POLYETHER POLYOL AND POLYURETHANE FOAM OBTAINED THEREFROM

[75] Inventors: Lawrence B. Barry, Newington; Mark C. Richardson, Cheshire, both of Conn.

[73] Assignee: Uniroyal Chemical Company, Inc., Middlebury, Conn.

[21] Appl. No.: 329,019

[22] Filed: Oct. 25, 1994

[51] Int. Cl.$^6$ .............. C08K 5/132; C08K 5/16; C09K 15/08; C09K 15/18

[52] U.S. Cl. .............. 252/400.24; 252/401; 252/404; 521/174; 524/128; 524/153; 568/581; 568/582; 564/409

[58] Field of Search .............. 252/400.24, 401, 252/404; 564/409; 524/128, 153; 568/581, 582; 521/174

[56] References Cited

U.S. PATENT DOCUMENTS

| | | | |
|---|---|---|---|
| 2,776,994 | 1/1957 | Wolf et al. | 564/433 |
| 2,943,112 | 6/1960 | Popoff et al. | 564/409 |
| 3,496,230 | 2/1970 | Kaplan | 564/409 |
| 3,497,457 | 2/1970 | Hurlock et al. | 252/182.24 |
| 3,649,690 | 3/1972 | Wheeler | 560/59 |
| 3,655,559 | 4/1972 | Holt | 252/51.5 A |
| 3,714,257 | 1/1973 | Bayha | 564/409 |
| 3,714,258 | 1/1973 | Bayha et al. | 564/409 |
| 3,758,519 | 9/1973 | Wheeler | 564/315 |
| 3,886,114 | 5/1975 | Beadle | 528/128 |
| 4,169,196 | 9/1979 | Ehrlich et al. | 528/58 |
| 4,520,149 | 5/1985 | Golder | 524/100 |
| 4,704,219 | 11/1987 | Shaw | 252/50 |
| 4,707,509 | 11/1987 | Fisch et al. | 524/147 |
| 4,739,121 | 4/1988 | Shaw | 564/409 |
| 4,824,601 | 4/1989 | Franklin | 252/401 |
| 4,973,759 | 11/1990 | Klein et al. | 564/437 |
| 5,015,679 | 5/1991 | Matumara | 524/99 |
| 5,155,153 | 10/1992 | Neri et al. | 524/101 |
| 5,186,852 | 2/1993 | Ishida et al. | 252/50 |
| 5,214,211 | 5/1993 | Karek et al. | 564/409 |
| 5,219,892 | 6/1993 | Suhoza | 521/107 |
| 5,238,606 | 8/1993 | Downs et al. | 549/387 |
| 5,256,333 | 10/1993 | Barry et al. | 252/400.24 |
| 5,268,394 | 12/1993 | Wheeler et al. | 521/108 |
| 5,273,669 | 12/1993 | Schumacher et al. | 252/47.5 |
| 5,338,478 | 8/1994 | Barry et al. | 252/182.27 |

FOREIGN PATENT DOCUMENTS

| | | |
|---|---|---|
| 0350681 | 1/1990 | European Pat. Off. . |
| 846226 | 8/1960 | United Kingdom . |

*Primary Examiner*—Sharon Gibson
*Assistant Examiner*—Valerie Fee
*Attorney, Agent, or Firm*—Raymond D. Thompson

[57] ABSTRACT

A stabilizer composition useful as an additive for polyether polyols, particularly those employed in the manufacture of polyurethane foams, is provided which comprises a diphenylamine:isobutylene:diisobutylene reaction product, a sterically hindered phenol and a trihydrocarbyl phosphite.

8 Claims, No Drawings

STABILIZED POLYETHER POLYOL AND POLYURETHANE FOAM OBTAINED THEREFROM

BACKGROUND OF THE INVENTION

This invention relates to a stabilizer composition, to a polyether polyol stabilized against degradation by the stabilizer composition and to a polyurethane foam obtained from the stabilized polyether polyol.

U.S. Pat. No. 5,256,333 discloses the use of pentaerythritol diphosphite with diarylamines and sterically hindered phenol as a stabilizer for polyether polyols. U.S. Pat. No. 4,824,601 discloses the use as a stabilizer of organic materials of a diphenylamine/diisobutylene reaction product with the reactant ratio range of 1:1.1 to 1:2.5.

SUMMARY OF THE INVENTION

In accordance with the present invention, a stabilizer composition is provided which comprises:

a) a diphenylamine:isobutylene:diisobutylene reaction product wherein the overall molar ratios of diphenylamine:isobutylene:diisobutylene reactants are 1:0.5 to 1.3:0.75 to 1.3;

b) a sterically hindered phenol; and c) a trihydrocarbyl phosphite compound.

The foregoing stabilizer composition is especially useful as an additive for polyether an polyester polyols, particularly those employed in the manufacture of polyurethane foams where it further serves to prevent or reduce discoloration and scorching of the foamed products. This invention provides the following advantages over those currently in use:

a) reduced handling;

b) increased hydrolytic stability as compared to other liquid phosphites containing stabilizer systems;

c) reduced processing time due to elimination of filtration step;

d) increased color stability of stabilizer composition due to addition of phosphite.

e) faster blending times of the stabilizer composition and the polyether polyol;

f) reduction of color in the antioxidant blend;

g) reduction of color formation of flexible polyurethane foam during manufacture.

h) reduction of color formation of flexible polyurethane foam during storage.

DESCRIPTION OF THE PREFERRED EMBODIMENTS

The alkylated diphenylamine useful in this invention is a unique, specialized reaction product of diphenylamine:isobutylene:diisobutylene. The terms "reaction product" or "reaction product of diphenylamine:isobutylene:diisobutylene" or "DPA:IB:DIB reaction product" as used herein shall refer to this specialized two-stage reaction product which is an advancement in the art of alkylated diphenylamines. The preferred method of making this specialized reaction product is: diphenylamine and isobutylene are added in a first reaction stage at a temperature of 140° C. or lower in the presence Of an activated earth catalyst to form a first stage DPA:IB (diphenylamine:isobutylene) reaction product. The amount of DPA to isobutylene in the first stage is greater than the 1:2 stoichiometric ratio, thereby leaving residual DPA reaction sites still unreacted going into the second stage.

In the second stage, diisobutylene is added to the first stage reaction product, preferably with additional catalyst, to form the finished reaction product of DPA:isobutylene:diisobutylene. Additional isobutylene may also optionally be added to the second stage reaction along with the diisobutylene. The molar ratio ranges of the diphenylamine:isobutylene:diisobutylene reactants are 1:0.5 to 1.3:0.75 to 1.3 across the complete two stage reaction scheme. Preferred DPA:IB:DIB ratio range is 1:0.7 to 1.2:0.9 to 1.1. More preferred ratio range is 1:0.9 to 1.1:1.0 to 1.1

The activated earth catalysts are preferably utilized. The sulfuric acid activated Fuller's earth or the acid bleached Bentonite clays or the Montmorillinite clays are also useful, all with acid treatment. This unique two-stage reaction product yields a substituted diphenylamine uniquely suited to the stabilization of polyols or as a lubricant additive. Other aspects of the process of manufacturing this alkylated diphenylamine are conventional in the well known art of alkylated diphenylamine products. The two stage reaction product exhibits excellent color and well defined fractions of butyl, dibutyl, butyloctyl, and dioctyl substituted DPA diphenylamines visa vis other conventionally produced alkyl-substituted diphenylamines.

The diphenylamine:isobutylene/diphenylamine:diisobutylene reaction product component of the stabilizer composition of this invention can be present therein in widely varying amounts, e.g., from about 10 to about 90, preferably from about 20 to about 70, and most preferably from about 30 to about 60, weight percent based on the entire weight of stabilizer composition.

Other diarylamines with antioxidant/stabilization protection may be useful including a diarylamine selected from the group consisting of a diphenylamine:isobutylene:diisobutylene reaction product, diphenylamine, p,p'-di-tert-octyldiphenylamine, p,p'-di-α-phenylethyldiphenylamine, p-tert-octyl-p'-phenylethyl-diphenylamine, p-tert-octyldiphenylamine, p-phenylethyldiphenylamine, tri-t-octyldiphenylamine, p-tert-butyldiphenylamine, p,p'-di-tert-butyldiphenylamine, p-tert-octyl-p'-butyldiphenylamine, p-tert-butyl-p'-phenylethyldiphenylamine, phenyl-beta-diphenylamine, the ditolylamines, the phenyltolylamines, the dinaphthylamines, dianilinodiphenylmethane, p-hydroxyldiphenylamine, p-amino-diphenylamine, N,N'-diphenyl-p-phenylenediamine, p-chlorodiphenylamine, p-isopropoxydiphenylamine, 4,4'-bis-(αα-dimethylbenzyl)diphenylamine, 4,4'-bis-(α-methylbenzyl)diphenylamine, α-dimethylbenzyl)diphenylamine and α-methylbenzyl diphenylamine.

Suitable hindered phenols that can be utilized in the liquid stabilizer composition herein include 2,4-dimethyl-6-octylphenol, 2,6-di-t-butyl-4-methylphenol, 2,6-di-t-butyl-4-nonylphenol, 2,6-di-t-butyl-4-ethylphenol, 2,6-di-t-butyl-4-n-butylphenol, 2,6-di-t-butyl-4-sec-butylphenol, 2,2'-methylenebis(4-methyl-6-t-butylphenol), 2,2'-methylenebis(4-ethyl-6-t-butylphenol), 2,4-dimethyl-6-t-butylphenol, 4-hydroxymethyl-2,6-di-t-butylphenol, n-octadecyl-β(3,5 di-t-butyl-4-hydroxyphenyl)propionate, 4,4'-dihydroxydiphenol, 4,4'-thiobis(6-t-butyl-o-cresol), p-butylphenol, p-isopropylphenol, p-(1,1,3,3-tetramethylbutyl)phenol, 2,6-dioctadecyl-4-methyl phenol; 2,4,6-trimethyl phenol; 2,4,6-triisopropyl phenol; 2,4,6-tri-tert-butyl phenol; 2-tert-butyl-4,6-dimethyl phenol; 2,6-methyl-4-didodecyl phenol; octadecyl-3,5-di-tert-butyl-4-hydroxy hydrocinnamate; tetrakis

[methylene (3,5-di-tert-butyl-4-hydroxy-hydrocinnamate)] methane; 2,2'-oxamido bis-[ethyl-3-(3,5-di-tert-butyl-4-hydroxyphenyl)propionate; 1,3,5-tris(4-tert-butyl-3-hydroxy-2,6-dimethylbenzyl)-s-triazine-2,4,6-(1H, 3H, 5H)trione; 1,3,5-trimethyl-2,4,6-tris(3, 5-di-tert-butyl-4-hydroxybenzyl)benzene; tris(3,5-di-tert-butyl-4-hydroxybenzyl) isocyanurate; thymol, mixed m- and p-cresol, p-nonylphenol, other phenols, cresols having alkyl substituents and mixtures thereof.

A preferred hindered phenol is 2,6-di-t-butyl-4-sec-butylphenol. The hindered phenol component of the stabilizer composition of this invention can be present therein in widely varying amounts, e.g., from about 10 to about 90, preferably from about 40 to about 80, and most preferably from about 50 to about 70, weight percent based on the entire weight of stabilizer composition.

The trihydrocarbyl phosphites that can be utilized in the stabilizer composition herein are of the structure below:

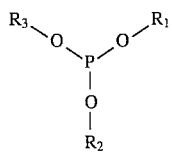

wherein $R_1$, $R_2$, and $R_3$ may be the same or different selected from $C_8$–$C_{15}$ alkyl, phenyl and phenyl substituted with $C_8$–$C_{12}$ alkyl containing from 8 to 12 carbon atoms. All alkyl groups may be cyclic, branched or straight chain. Preferably, the trihydrocarbyl phosphite is substituted with $R_1$, $R_2$, and $R_3$ Of both alkyl and aryl groups. Still more preferably, the alkyl groups contain from 9 to 12 carbon atoms, and one substituent is phenyl.

Examples of such currently employed phosphites are triisodecyl phosphite, trilauryl phosphite, diphenyl isodecyl phosphite, phenyl diisodecyl phosphite, triphenyl phosphite, tris(mono-nonyl-phenyl)phosphite and triis(2,3-di-t-butylphenyl) phosphite.

In a preferred embodiment of this invention, a preferred trihydrocarbyl phosphite is phenyl diisodecyl phosphite. In this composition, $R_1$ and $R_2$ are both $C_{10}H_{21}$ and $R_3$ is phenyl. This compound is commercially available and as is sold by General Electric as Weston PDDP Phosphite. This substance will be referred to as PDDP in this disclosure.

Of the three components of the stabilizer composition herein, the trihydrocarbyl phosphite component will generally be present in the lowest amount, e.g., from about 0.1 to about 10, preferably from about 1 to about 8, and most preferably from about 3 to about 5 weight percent based on the entire weight of stabilizer composition.

As previously indicated, the stabilizer composition of this invention is particularly useful for the stabilization of polyether polyols, primarily from degradation resulting from oxidation. Throughout this specification, the term "polyether polyols" shall include polyester polyols which are structurally and chemically similar although generally having slightly lesser tendencies to degrade than the polyether types. The polyether polyols are well known in the art and are obtained by reacting polyhydric alcohols, e.g., those containing from 2–8 hydroxyl groups such as ethylene glycol, propylene glycol, diethylene glycol, 2,3-butylene glycol, 1,3-butylene glycol, 1,5-pentane diol, glycerol, trimethylolpropane, triethylolpropane, sorbitol, pentaerythritol, and mixtures thereof, with a 1,2-epoxide, e.g., ethylene oxide, propylene oxide, butylene oxide, cyclohexane oxide, glycidol and the halogenated alkylene oxides such as 4,4,4-trichloro-1,2-epoxybutane, and mixtures thereof. The preferred polyether polyols contain from 2–4 hydroxyl groups and are obtained by reacting one or more polyhydric alcohols having a like number of hydroxyl groups with ethylene oxide, propylene oxide, butylene oxide, and mixtures thereof.

The stabilizer composition is added to the polyether polyol in an effective amount sufficient to impart an appreciable stabilizing effect. In general, this amount may vary from about 0.1 to about 2 weight percent, preferably from about 0.2 to about 1 weight percent and most preferably from about 0.4 to about 0.6 weight percent by total weight of polyether polyol(s). Where the polyether polyol is to be employed in the manufacture of a polyurethane foam and stabilization of the polyol is not an issue, the stabilizer composition may be added to some other component of the polyurethane-forming reaction mixture, e.g., to the polyisocyanate, prepolymer, foaming agent, etc., or to the reaction mixture once formed, rather than to the polyol. In this case, the foregoing amounts of stabilizer composition calculated on the basis of the total polyether polyol component can be utilized.

Any suitable organic isocyanate which is capable of reacting with a polyether polyol to form a polyurethane can be employed in preparing the foam. This includes diisocyanates and polyisocyanates, e.g., triisocyanates and polymeric isocyanates. Due to their commercial availability, the polymeric isocyanates and tolylene diisocyanate are preferred. The latter, the use of which is more preferred, can be supplied in the form of an isomeric mixture of about 80 weight percent of 2,4-isomer and about 20 weight percent of 2,6-isomer. Other typical isocyanates include 4,4'-methylene-bis(phenylisocyanate), 3,3'-bitolylene-4,4'-diisocyanate, 3,3'-dimethoxy-biphenylene- 4,4'-diisocyanate, naphthalene- 1,5-diisocyanate, hexamethylene diisocyanate, 1,4-phenylene diisocyanate, polyphenylene polymethylene isocyanate, etc. The amount of isocyanate employed in the preparation of the polyurethane foams should be sufficient to provide at least about 0.7 NCO groups per hydroxyl group present in the reaction system. An excess of isocyanate compound can be conveniently employed; however, the use of a large excess is generally undesirable due to the high cost of the isocyanate compounds. It is preferable, therefore, to employ no greater than about 1.5 NCO groups per hydroxyl group, and still more preferably from about 0.9 to about 1.3 NCO groups per hydroxyl group.

In preparing the polyurethane foams, the polyether polyol is reacted with the organic isocyanate in the presence of a foaming agent and a reaction catalyst. The foaming agent can be any one of those known to be useful for this purpose, such as water, which is preferred, the halogenated hydrocarbons and mixtures thereof. Typical halogenated hydrocarbons include monofluorotrichloromethane, difluorodichloromethane, 1,1,2-trichloro-1,2,2-trifluoroethane, methylene chloride, etc. The amount of foaming agent employed can be varied within a wide range. Generally, however, the halogenated hydrocarbons are employed in an amount from about 1 to about 50 parts by weight per 100 parts by weight of the polyether polyol, and generally water is employed in an amount of from about 0.1 to about 10 parts by weight per 100 parts by weight of the polyether polyol.

The catalyst used in preparing the polyurethane foams can be any one of those known to be useful for this purpose or mixtures thereof, including tertiary amines and metallic salts. Typical tertiary amines include N-methyl morpholine, N-hydroxyethyl morpholine, triethylene diamine, dimethyl ethanolamine, tetramethylbutane diamine, trimethylamine, triethylamine, etc. Typical metallic salts include the salts of antimony, tin and iron, e.g., dibutyltin dilaurate, stannous octoate, etc. Generally speaking, the catalyst is employed in an amount ranging from about 0.1 to about 2.0 weight percent based on the weight of the polyether polyol.

It is preferred in the preparation of the polyurethane foams of the present invention to employ minor amounts of a surfactant in order to improve the cell structure of the polyurethane foams. Typical of such surfactants are the silicon-based surfactants as disclosed, e.g., in U.S. Pat. No. 2,834,748 and in the book "Rigid Plastic Foams" by T. H. Ferrigno (1963), Reinhold Publishing Company. Other suitable compounds useful as surfactants include synthetic detergents such as oxyethylated nonyl phenol and other ethylene oxide and glycidol-based surfactants. Generally up to about 2 parts by weight of the surfactant is employed per 100 parts by weight of polyether polyol.

Various additives can also be employed in preparing the foam which serve to provide different properties. Fillers, e.g., clay, calcium sulfate, barium sulfate, ammonium phosphate, etc., can be added to lower cost and improve physical properties. Dyes can be added for color and fibrous glass, asbestos, or synthetic fibers can be added for strength. In addition, plasticizer, deodorants and flame retardants can be added.

Among the advantages of using the trihydrocarbyl phosphites of this invention as compared to prior known use of other solid diphosphites are the total liquid composition of the stabilizer composition. Because all ingredients are liquids, the blending of total liquid stabilizer system may be carried out in the absence of heat. This leads to faster blending times, no cool-down period required once blending has been completed. Easier filtration results from the absence of solid particles in the system.

Use of the trihydrocarbyl phosphites in the composition of the instant invention promotes color reduction in said composition. In a preferred embodiment, the trihydrocarbyl phosphite promoting color reduction is PDDP. Similarly, use of this and similar trihydrocarbyl phosphites results in the reduction of color formation of the final product flexible polyurethane and polyester flexible foam.

The use of the trihydrocarbyl phosphites of this invention has been proven to be particularly effective at reducing color and preventing color development in amine and phenolic antioxidant blends. Antioxidant blends containing phenolic antioxidants based on 2,6-di-t-butyl-4-alkyl phenol and the amine reaction product of DPA:IB:DIB were particularly improved by the incorporation of the trihydrocarbyl phosphite compounds of this invention, resulting in lightening of the stabilizer composition A final advantage is the costs involved. The trihydrocarbyl phosphites of the instant invention are less costly than some of the solid diphosphites.

The following examples are illustrative of the invention, and are not intended to limit its scope in any manner whatsoever.

COMPARATIVE EXAMPLE A AND B AND EXAMPLE 1–8

Color Testing Procedure

Sample Preparation: Samples were prepared by adding approximately 100 grams of antioxidant to 4 oz glass sample bottles at room temperature. The samples were then mixed and immediately measured via the Gardner Color Measurement System for color. The samples were then heated to 70° C. in an air circulating oven for one hour with occasional mixing and then measured again for color. The samples were then allowed to stand for two days at room temperature and again measured for color. It should be noted that the amount of discoloration present in the various samples, measured via the Gardner Color Measurement System, is a subjective test and is subject to operator interpretation. The lower numbers indicate less color and are preferred.

Results of the color testing procedures are shown in Table I. The antioxidants used and the appropriate amounts are indicated.

TABLE I

RESULTS - COLOR TESTING

| % ANTIOXIDANT | COMPARATIVE | | FORMULATIONS | | | | | | | |
|---|---|---|---|---|---|---|---|---|---|---|
| | A | B | 1 | 2 | 3 | 4 | 5 | 6 | 7 | 8 |
| DPA:IB:DIB REACTION PRODUCT | 100 | 90 | 40 | 40 | 40 | 40 | 40 | 40 | 40 | 40 |
| PHENOLIC 1 | — | — | 55 | — | — | — | 55 | 55 | 55 | 55 |
| PHENOLIC 2 | — | — | — | 55 | — | — | — | — | — | — |
| PHENOLIC 3 | — | — | — | — | 55 | — | — | — | — | — |
| PHENOLIC 4 | — | — | — | — | — | 55 | — | — | — | — |
| PHOSPHITE PDDP | — | 10 | 5 | 5 | 5 | 5 | — | — | — | — |
| PHOSPHITE DPDP | — | — | — | — | — | — | 5 | — | — | — |
| PHOSPHITE TDP | — | — | — | — | — | — | — | 5 | — | — |
| PHOSPHITE TPP | — | — | — | — | — | — | — | — | 5 | — |
| PHOSPHITE TIOP | — | — | — | — | — | — | — | — | — | 5 |
| EXPERIMENTAL RESULTS | | | | | | | | | | |
| INITIAL GARDNER COLOR | 5 | 4 | 3 | 3 | 3 | 3 | 3 | 3 | 3 | 3 |
| AFTER 1 HR @ 70° C. | 5 | 2 | 1 | 1 | 1 | 1 | 1 | 1 | 1 | 1 |
| AFTER 2 DAYS @ ROOM TEMP. | 5 | 2 | 1 | 1 | 3 | 1 | 1 | 1 | 1 | 1 |

Antioxidants used were the diphenylamine:isobutylene:diisobutylene reaction product described earlier (DPA:IB:DIB reaction product), Phenolic 1=(2,6-di-t-butyl-4-sec-butyl-phenol), Phenolic 2=(2,6-di-t-butyl-4-nonyl-phenol), Phenolic 3=(alkylated p-cresol), Phenolic 4 =alkylated 2,6-di-t-butyl phenol available from Uniroyal Chemical Company, Inc. as Naugard™ PS-40, Phosphite TDP=(triisodecyl phosphite), Phosphite DPDP=(diphenyl isodecyl phosphite), Phosphite PDDP=(phenyl diisodecyl phosphite), Phosphite TPP=(triphenyl phosphite), Phosphite TIOP=(triisooctyl phosphite).

Comparative Example A shows that the Reaction Product when used alone has a poor initial and aged color of 5. Comparative Example B shows that the Reaction Product even with the best trihydrocarbyl phosphite has a poor initial color of 4 and aged color of 2. The above data show that the stabilizer composition containing all three components of this invention (Examples 1 through 8) lighten markedly after a one hour period subsequent to mixing the stabilizer. The stabilizer compositions are lighter in color after two days of aging demonstrating that the effect is not transient.

EXAMPLE 9

The stabilizer formulation of Example 1 was incorporated into a polyether polyol and exposed to air and sunlight over an eight week period. The Gardner color rating was 2 at the end of the eight week exposure indicating excellent long term stability of the color improvement shown in Table I.

INDUSTRIAL APPLICABILITY

This marked improvement in color is a significant advantage to polyol manufacturers and represents a significant step forward in the crowded art field of stabilization, where very small improvements are important where they address a long standing problem, such as the one successfully addressed here, the tendency of alkylated diphenylamine stabilizers tend to show dark colors and tend to build color bodies in the polyol over long storage intervals. This invention successfully deals with this problem.

The above preferred embodiments and examples are given to illustrate the scope of the present invention. These preferred embodiments and examples will make apparent, to those skilled in the art, other embodiments and examples. These other embodiments and examples are within the contemplation of the subject invention. Therefore, the scope of the present invention should be limited only by the appended claims.

What is claimed is:

1. A liquid stabilizer composition comprising:
    a) from about 30 to about 50 weight percent of a diphenylamine:isobutylene:diisobutylene reaction product;
    b) from about 50 to about 70 weight percent of a hindered phenol; and,
    c) from about 1 to about 8 weight percent of a trihydrocarbyl phosphite;
wherein the molar ratio ranges of the diphenylamine:isobutylene:diisobutylene reactants in said reaction product are 1:0.5 to 1.3:0.75 to 1.3, said reaction product being formed at a temperature of 140° C. or lower in the presence of an acid activated earth catalyst.

2. The liquid stabilizer composition of claim 1 wherein the trihydrocarbyl phosphite is phenyl diisodecyl phosphite.

3. The liquid stabilizer composition of claim 1 wherein the hindered phenol is selected from the group consisting of 2,4-dimethyl-6-octylphenol, 2,6-di-t-butyl-4-methylphenol, 2,6-di-t-butyl-4-nonylphenol, 2,6-di-t-butyl- 4-n-butylphenol, 2,6-di-t-butyl-4-ethylphenol, 2,6-di-t-butyl-4-sec-butylphenol, 2,2'-methylenebis(4-methyl-6-t-butylphenol), 2,2'-methylenebis( 4-ethyl-6-t-butylphenol), 2,4-dimethyl-6-t-butylphenol, 4-hydroxymethyl- 2,6-di-t-butylphenol, n-octadecyl-β(3,5 di-t-butyl-4-hydroxyphenyl)propionate, 4,4'-dihydroxydiphenol, 4,4'-thiobis(6-t-butyl-o-cresol), p-butylphenol, p-isopropylphenol, p-(1,1,3,3-tetramethylbutyl)phenol, 2,6-dioctadecyl-4-methyl phenol; 2,4,6-trimethyl phenol; 2,4,6-triisopropyl phenol; 2,4,6-tri-tert-butyl phenol; 2-tert-butyl-4,6-dimethyl phenol; 2,6-methyl-4-didodecyl phenol; octadecyl-3,5-di-tert-butyl-4-hydroxy hydrocinnamate; tetrakis[methylene (3,5-di-tert-butyl-4-hydroxyhydrocinnamate)]methane; 2,2'-oxamido bis-[ethyl-3-(3,5-di-tert-butyl-4-hydroxyphenyl)propionate; 1,3,5-tris(4-tert-butyl-3-hydroxy-2,6-dimethylbenzyl)-s-triazine- 2,4,6-(1H,3H,5H)trione; 1,3,5-trimethyl-2,4,6-tris(3,5 -di-tert-butyl-4-hydroxybenzyl)benzene; tris(3,5-di-tert-butyl-4-hydroxybenzyl)isocyanurate; thymol, mixed m- and p-cresol, p-nonylphenol and mixtures thereof.

4. A polyether polyol stabilized against degradation by the inclusion therein of a stabilizing amount of the liquid stabilizer composition of claim 1.

5. The polyether polyol of claim 4 wherein the liquid stabilizer composition is present therein in an amount of from about 0.1 to about 2 weight percent by total weight of the polyether polyol.

6. The polyether polyol of claim 4 wherein the liquid stabilizer composition is present therein in an amount of from about 0.2 to about 1 weight percent by total weight of polyether polyol.

7. The polyether polyol of claim 4 wherein the liquid stabilizer composition is present therein in an amount of from about 0.4 to about 0.6 weight percent by total weight of the polyether polyol.

8. A polyurethane foam comprising: a polyether polyol reacted with the organic isocyanate in the presence of a foaming agent and a reaction catalyst, said polyether polyol having incorporated therein a liquid stabilizer composition comprising:
    a) from about 30 to about 50 weight percent of a diphenylamine:isobutylene:diisobutylene reaction product;
    b) from about 50 to about 70 weight percent of a hindered phenol; and,
    c) from about 1 to about 8 weight percent of a trihydrocarbyl phosphite;
wherein the molar ratio ranges of the diphenylamine:isobutylene:diisobutylene reactants in said reaction product are 1:0.5 to 1.3:0.75 to 1.3, said reaction product being formed at a temperature of 140° C. or lower in the presence of an acid activated earth catalyst.

* * * * *